(12) United States Patent
Bryan et al.

(10) Patent No.: US 7,250,170 B2
(45) Date of Patent: Jul. 31, 2007

(54) OPTIMIZED EXPRESSION OF HPV 45 L1 IN YEAST

(75) Inventors: Janine T. Bryan, Furlong, PA (US); Michelle K. Brownlow, Jamison, PA (US); Loren D. Schultz, Harleysville, PA (US); Kathrin U. Jansen, Allendale, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/573,330

(22) PCT Filed: Sep. 24, 2004

(86) PCT No.: PCT/US2004/031326

§ 371 (c)(1), (2), (4) Date: Mar. 24, 2006

(87) PCT Pub. No.: WO2005/032586

PCT Pub. Date: Apr. 14, 2005

(65) Prior Publication Data

US 2006/0240040 A1 Oct. 26, 2006

Related U.S. Application Data

(60) Provisional application No. 60/506,812, filed on Sep. 29, 2003.

(51) Int. Cl.
*A61K 39/12* (2006.01)

(52) U.S. Cl. .............................. 424/204.1; 424/199.1; 435/91.1; 435/69.1

(58) Field of Classification Search ............. 424/204.1, 424/199.1; 435/91.1, 325, 69.1, 320.1
See application file for complete search history.

(56) References Cited

U.S. PATENT DOCUMENTS

2004/0121465 A1* 6/2004 Robinson ..................... 435/456

FOREIGN PATENT DOCUMENTS

| WO | WO 96/15247 | 5/1996 |
| WO | WO 98/34640 | 8/1998 |
| WO | WO 99/02694 | 1/1999 |
| WO | WO 01/14416 A2 | 3/2001 |
| WO | WO 01/41799 A1 | 6/2001 |
| WO | WO 02/08435 A1 | 1/2002 |
| WO | WO 03/077942 A2 | 9/2003 |
| WO | WO 2004/084831 A2 | 10/2004 |

OTHER PUBLICATIONS

Bosch, et al., "Prevalence of Human Papillomavirus in Cervical Cancer: a Worldwide Perspective", J. Nat. Cancer Inst., vol. 87, No. 11, Jun. 7, 1995, pp. 796-802.
Breitburd, et al., "Immunization with Viruslike Particles from Cottontail Rabbit Papillomavirus (CRPV) Can Protect Against Experimental CRPV Infection", J. of Virol., vol. 69, No. 6, Jun. 1995, pp. 3959-3963.
Delius, et al., "Primer-Directed Sequencing of Human Papillomavirus Types", Curr. Topics in Microbiology. and Immunology, vol. 186, 1994, pp. 13-31.
GenBank Accession No. Q9Y4Y5, 1999.
Kortula, et al., "Evaluation of Foreign Gene Codon Optimization in Yeast: Expression of a Mouse IG Kappa Chain", Bio/Technology, vol. 9, Dec. 1991, pp. 1386-1389.
Liu, et al., "Polynucleotide viral vaccines: codon optimization and ubiquitin conjugation enhances prophylactic and therapeutic efficacy", Vaccine, vol. 20, 2002, pp. 862-869.
McMurray, et al., "Biology of human papillomaviruses", International Journal of Experimental Pathology, vol. 82, 2001, pp. 15-33.
Neeper, et al., "Expression of the major capsid protein of human papillomavirus type 11 in *Saccharomyces cerevisae*", Gene, vol. 180, 1996, pp. 1-6.
Schiffman, et al., "Epidemiologic Evidence Showing That Human Papillomavirus Infection Causes Most Cervical Intraepithelial Neoplasia", Journal of National Cancer Institute, vol. 85, No. 12, Jun. 16, 1993, pp. 958-964.
Schiller, et al., "Developing HPV virus-like particle vaccines to prevent cervical cancer: a progress report", Journal of Clinical Virology, vol. 19, 2000, pp. 67-74.
Schiller, et al., "Papillomavirus-Like Partcles: Basic and Applied Studies", Papillomavirus Reviews: Current Research on Papillomavirus, ed. Leeds, UK: Leeds Medical Information, 1996, pp. 101-112.
Sharp, et al., "Synonymous Codon Usage in *Saccharomyces cerevisiae*", Yeast, vol. 7, 1991, pp. 657-678.
Suzich, et al., "Systemic immunization with papillomavirus L1 protein completely prevents the development of viral mucosal papillomavirus", PNAS, vol. 92, Dec. 1995, pp. 11553-11557.
Tobery, et al., "Effect of vaccine delivery system on the induction of HPV 16 L1-specific humoral and cell-mediated immune responses in immunized rhesus macaques", Vaccine, vol. 21, 2003, pp. 1539-1547.
Zhou, et al., "Papillomavirus Capsid Protein Expression Level Depends on the Match between Codon Usage and tRNA Availability", J. of Virol., vol. 73, No. 6, Jun. 1999, pp. 4972-4982.

* cited by examiner

*Primary Examiner*—Ali R. Salimi
(74) *Attorney, Agent, or Firm*—Alysia A. Finnegan; Sheldon O. Heber

(57) ABSTRACT

Synthetic DNA molecules encoding the HPV45 L1 protein are provided. Specifically, the present invention provides polynucleotides encoding HPV45 L1 protein, wherein said polynucleotides have been codon-optimized for high level expression in a yeast cell. The synthetic molecules may be used to produce HPV45 virus-like particles (VLPs), and to produce vaccines and pharmaceutical compositions comprising the HPV45 VLPs. The vaccines of the present invention provide effective immunoprophylaxis against papillomavirus infection through neutralizing antibody and cell-mediated immunity.

8 Claims, 10 Drawing Sheets

HPV 45 L1 Nucleotide Sequence Alignment

```
45 L1 wt   (   1)  ATGGCTTTGTGGCGGCCTAGTGACAGTACGGTATATCTTCCACCACCTTC
45 L1 R    (   1)  ............A.A..ATC....TC...T..C..CT.G........A..

45 L1 wt   (  51)  TGTGGCCAGAGTTGTCAACACTGATGATTATGTGTCTCGCACAAGCATAT
45 L1 R    (  51)  ...C..T.....C...........C..C..C..C..CA.A..CTC...C.

45 L1 wt   ( 101)  TTTACCATGCAGGCAGTTCCCGATTATTAACTGTAGGCAATCCATATTTT
45 L1 R    ( 101)  .C.....C..T..TTC....A....G..G.....C..T..C.....C..C

45 L1 wt   ( 151)  AGGGTTGTACCTAGTGGTGCAGGTAATAAACAGGCTGTTCCTAAGGTATC
45 L1 R    ( 151)  ..A..C..C..ATCC.....T.....C..G..A........A.....C..

45 L1 wt   ( 201)  CGCATATCAGTATAGGGTGTTTAGAGTAGCTTTGCCCGATCCTAATAAAT
45 L1 R    ( 201)  T..T..C..A..C..A..C..C.....C........A..C..A..C..G.

45 L1 wt   ( 251)  TTGGATTACCTGATTCTACTATATATAATCCTGAAACACAACGTTTGGTT
45 L1 R    ( 251)  .C..T..G..A..C........C..C..C..A.....T...A.A.....C

45 L1 wt   ( 301)  TGGGCATGTGTAGGTATGGAAATTGGTCGTGGGCAGCCTTTAGGTATTGG
45 L1 R    ( 301)  ........C..C...........C...A.A..T..A..A..G.....C..

45 L1 wt   ( 351)  CCTAAGTGGCCATCCATTTTATAATAAATTGGATGATACAGAAAGTGCTC
45 L1 R    ( 351)  TT.GTC...T..C.....C..C..C..G.....C..C..C...TCC....

45 L1 wt   ( 401)  ATGCAGCTACAGCTGTTATTACGCAGGATGTTAGGGATAATGTGTCAGTT
45 L1 R    ( 401)  .C..T.....T.....C..C..T..A..C..C...A..C..C..C..T..C

45 L1 wt   ( 451)  GATTATAAGCAAACACAGCTGTGTATTTTAGGTTGTGTACCTGCTATTGG
45 L1 R    ( 451)  ..C..C........C...AT........C...G........C..A.....C..

45 L1 wt   ( 501)  TGAGCACTGGGCCAAGGGCACACTTTGTAAACCTGCACAATTGCAACCTG
45 L1 R    ( 501)  ...A........T.....T..CT.G.....G..A..T..........A.

45 L1 wt   ( 551)  GTGACTGTCCTCCTTTGGAACTTAAAAACACCATTATTGAGGATGGTGAT
45 L1 R    ( 551)  ..........A..A......T.G..G.....T..C..C..A..C.....C
```

FIG.1A

```
45 L1 wt   ( 601)  ATGGTGGATACAGGTTATGGGGCAATGGATTTTAGTACATTGCAGGATAC
45 L1 R    ( 601)  .....T..C..T.....C..T..T.....C..CTCC..CC.......C..

45 L1 wt   ( 651)  AAAGTGCGAGGTTCCATTAGACATTTGTCAATCCATCTGTAAATATCCAG
45 L1 R    ( 651)  T.....T..A........G.....C........T........G..C....

45 L1 wt   ( 701)  ATTATTTGCAAATGTCTGCTGATCCCTATGGGGATTCTATGTTTTTTTGC
45 L1 R    ( 701)  .C..C...........C.....C..A..C..T..C........C..C..T

45 L1 wt   ( 751)  CTACGCCGTGAACAACTGTTTGCAAGACATTTTTGGAATAGGGCAGGTGT
45 L1 R    ( 751)  T.GA.AA.A......T....C..T.....C..C.....C..A..T.....

45 L1 wt   ( 801)  TATGGGTGACACAGTACCTACAGACCTATATATTAAAGGCACTAGCGCTA
45 L1 R    ( 801)  C...........T..T..A..T...T.G..C..C..G..T..CTCT....

45 L1 wt   ( 851)  ATATGCGTGAAACCCCTGGCAGTTGTGTGTATTCCCCTTCTCCCAGTGGC
45 L1 R    ( 851)  .C...A.A.....T..A..TTCC.....C..C..T..A.....ATC...T

45 L1 wt   ( 901)  TCTATTACTACTTCTGATTCTCAATTATTTAATAAGCCATATTGGTTACA
45 L1 R    ( 901)  .....C........C...C........G..C..C........C.....G..

45 L1 wt   ( 951)  TAAGGCCCAGGGCCATAACAATGGTATTTGTTGGCATAATCAGTTGTTTG
45 L1 R    ( 951)  C.....T..A..T..C.....C.....C........C..C..A.....C.

45 L1 wt   (1001)  TTACTGTAGTGGACACTACCCGCAGTACTAATTTAACATTATGTGCCTCT
45 L1 R    (1001)  .C..C..C..T........A.ATC......C..G..C..G.....T...

45 L1 wt   (1051)  ACACAAAATCCTGTGCCAAATACATATGATCCTACTAAGTTTAAGCACTA
45 L1 R    (1051)  ...T.....C..A..T.....C..T..C..C..A..C.....C........

45 L1 wt   (1101)  TAGTAGACATGTGGAGGAATATGATTTACAGTTTATTTTTCAGTTGTGCA
45 L1 R    (1101)  CTCC.....C..C........C..C..G..A..C..C..C..A.....T.

45 L1 wt   (1151)  CTATTACTTTAACTGCAGAGGTTATGTCATATATCCATAGTATGAATAGT
45 L1 R    (1151)  ....C..C..G..C..T..A..C.....C..C..T..CTC......CTCC

45 L1 wt   (1201)  AGTATATTGGAAAATTGGAATTTTGGTGTACCTCCACCACCTACTACAAG
45 L1 R    (1201)  TC...C........C.....C..C.....T..A........A..C..CTC
```

FIG.1B

```
45 L1 wt    (1251)   TTTAGTGGATACATATCGTTTTGTGCAATCAGTTGCTGTTACCTGTCAAA
45 L1 R     (1251)   C..G..T..C..T..CA.A..C..C.....T..C.....C..T.......

45 L1 wt    (1301)   AGGATACTACACCTCCAGAAAAGCAGGATCCATATGATAAATTAAAGTTT
45 L1 R     (1301)   ....C..C..T..A..........A..C.....C..C..G..G.....C

45 L1 wt    (1351)   TGGACTGTTGACCTAAAGGAAAAATTTTCCTCCGATTTGGATCAATATCC
45 L1 R     (1351)   ...........T.G........G..C..T.....C.....C.....C..

45 L1 wt    (1401)   CCTTGGTCGAAAGTTTTTAGTTCAGGCTGGGTTACGTCGTAGGCCTACCA
45 L1 R     (1401)   AT.G...A.......C..G.....A.....T..GA.A.....A..A..T.

45 L1 wt    (1451)   TAGGACCTCGTAAGCGTCCTGCTGCTTCCACGTCTACTGCATCTAGGCCT
45 L1 R     (1451)   .C..T..A......A.A..A...........T..C.....T.....A..A

45 L1 wt    (1501)   GCCAAACGTGTACGTATACGTAGTAAAAAATAA (SEQ ID NO:3)
45 L1 R     (1501)   ..T..G.....CA.A..CA.ATCC..G..G...(SEQ ID NO:1)
```

FIG.1C

Synthetic HPV 45 L1 Nucleotide and Amino Acid Sequences

```
      M  A  L  W  R  P  S   D  S  T    V  Y  L  P   P  P  S
  1   ATGGCTTTGT GGAGACCATC TGACTCTACT GTCTACTTGC CACCACCATC
      TACCGAAACA CCTCTGGTAG ACTGAGATGA CAGATGAACG GTGGTGGTAG
      V  A  R   V  V  N  T   D  D  Y   V  S  R    T  S  I  F
 51   TGTCGCTAGA GTCGTCAACA CTGACGACTA CGTCTCCAGA ACCTCCATCT
      ACAGCGATCT CAGCAGTTGT GACTGCTGAT GCAGAGGTCT TGGAGGTAGA
      Y  H  A   G  S  S     R  L  L  T    V  G  N   P  Y  F
101   TCTACCACGC TGGTTCTTCC AGATTGTTGA CTGTCGGTAA CCCATACTTC
      AGATGGTGCG ACCAAGAAGG TCTAACAACT GACAGCCATT GGGTATGAAG
      R  V  V  P   S  G  A   G  N  K    Q  A  V  P   K  V  S
151   AGAGTCGTCC CATCCGGTGC TGGTAACAAG CAAGCTGTTC CAAAGGTCTC
      TCTCAGCAGG GTAGGCCACG ACCATTGTTC GTTCGACAAG GTTTCCAGAG
      A  Y  Q   Y  R  V  F   R  V  A    L  P  D    P  N  K  F
201   TGCTTACCAA TACAGAGTCT TCAGAGTCGC TTTGCCAGAC CCAAACAAGT
      ACGAATGGTT ATGTCTCAGA AGTCTCAGCG AAACGGTCTG GGTTTGTTCA
      G  L  P   D  S  T    I  Y  N  P    E  T  Q    R  L  V
251   TCGGTTTGCC AGACTCTACT ATCTACAACC CAGAAACTCA AAGATTGGTC
      AGCCAAACGG TCTGAGATGA TAGATGTTGG GTCTTTGAGT TTCTAACCAG
      W  A  C  V   G  M  E   I  G  R    G  Q  P  L   G  I  G
301   TGGGCATGCG TCGGTATGGA AATCGGTAGA GGTCAACCAT TGGGTATCGG
      ACCCGTACGC AGCCATACCT TTAGCCATCT CCAGTTGGTA ACCCATAGCC
      L  S  G   H  P  F  Y   N  K  L    D  D  T    E  S  A  H
351   TTTGTCTGGT CACCCATTCT ACAACAAGTT GGACGACACC GAATCCGCTC
      AAACAGACCA GTGGGTAAGA TGTTGTTCAA CCTGCTGTGG CTTAGGCGAG
      A  A  T   A  V  I     T  Q  D  V    R  D  N   V  S  V
401   ACGCTGCTAC TGCTGTCATC ACTCAAGACG TCAGAGACAA CGTCTCTGTC
      TGCGACGATG ACGACAGTAG TGAGTTCTGC AGTCTCTGTT GCAGAGACAG
      D  Y  K  Q   T  Q  L   C  I  L    G  C  V  P   A  I  G
451   GACTACAAGC AAACCCAATT GTGTATCTTG GGTTGTGTCC CAGCTATCGG
      CTGATGTTCG TTTGGGTTAA CACATAGAAC CCAACACAGG GTCGATAGCC
      E  H  W   A  K  G  T   L  C  K    P  A  Q    L  Q  P  G
501   TGAACACTGG GCTAAGGGTA CCTTGTGTAA GCCAGCTCAA TTGCAACCAG
      ACTTGTGACC CGATTCCCAT GGAACACATT CGGTCGAGTT AACGTTGGTC
```

FIG.2A

```
             D C P    P L E    L K N T    I I E    D G D
 551    GTGACTGTCC ACCATTGGAA TTGAAGAACA CTATCATCGA AGACGGTGAC
        CACTGACAGG TGGTAACCTT AACTTCTTGT GATAGTAGCT TCTGCCACTG
          M V D T    G Y G    A M D    F S T L    Q D T
 601    ATGGTTGACA CTGGTTACGG TGCTATGGAC TTCTCCACCC TGCAGGACAC
        TACCAACTGT GACCAATGCC ACGATACCTG AAGAGGTGGG ACGTCCTGTG
          K C E    V P L D    I C Q    S I C    K Y P D
 651    TAAGTGTGAA GTTCCATTGG ACATCTGTCA ATCTATCTGT AAGTACCCAG
        ATTCACACTT CAAGGTAACC TGTAGACAGT TAGATAGACA TTCATGGGTC
          Y L Q    M S A    D P Y G    D S M    F F C
 701    ACTACTTGCA AATGTCCGCT GACCCATACG GTGACTCTAT GTTCTTCTGT
        TGATGAACGT TTACAGGCGA CTGGGTATGC CACTGAGATA CAAGAAGACA
          L R R E    Q L F    A R H    F W N R    A G V
 751    TTGAGAAGAG AACAATTGTT CGCTAGACAC TTCTGGAACA GAGCTGGTGT
        AACTCTTCTC TTGTTAACAA GCGATCTGTG AAGACCTTGT CTCGACCACA
          M G D    T V P T    D L Y    I K G    T S A N
 801    CATGGGTGAC ACTGTTCCAA CTGACTTGTA CATCAAGGGT ACCTCTGCTA
        GTACCCACTG TGACAAGGTT GACTGAACAT GTAGTTCCCA TGGAGACGAT
          M R E    T P G    S C V Y    S P S    P S G
 851    ACATGAGAGA AACTCCAGGT TCCTGTGTCT ACTCTCCATC TCCATCTGGT
        TGTACTCTCT TTGAGGTCCA AGGACACAGA TGAGAGGTAG AGGTAGACCA
          S I T T    S D S    Q L F    N K P Y    W L H
 901    TCTATCACTA CTTCCGACTC TCAATTGTTC AACAAGCCAT ACTGGTTGCA
        AGATAGTGAT GAAGGCTGAG AGTTAACAAG TTGTTCGGTA TGACCAACGT
          K A Q    G H N N    G I C    W H N    Q L F V
 951    CAAGGCTCAA GGTCACAACA ACGGTATCTG TTGGCACAAC CAATTGTTCG
        GTTCCGAGTT CCAGTGTTGT TGCCATAGAC AACCGTGTTG GTTAACAAGC
          T V V    D T T    R S T N    L T L    C A S
1001    TCACCGTCGT TGACACTACC AGATCTACTA ACTTGACCTT GTGTGCTTCT
        AGTGGCAGCA ACTGTGATGG TCTAGATGAT TGAACTGGAA CACACGAAGA
          T Q N P    V P N    T Y D    P T K F    K H Y
1051    ACTCAAAACC CAGTTCCAAA CACTTACGAC CCAACCAAGT TCAAGCACTA
        TGAGTTTTGG GTCAAGGTTT GTGAATGCTG GGTTGGTTCA AGTTCGTGAT
          S R H    V E E Y    D L Q    F I F    Q L C T
1101    CTCCAGACAC GTCGAGGAAT ACGACTTGCA ATTCATCTTC CAATTGTGTA
        GAGGTCTGTG CAGCTCCTTA TGCTGAACGT TAAGTAGAAG GTTAACACAT
          I T L    T A E    V M S    Y I H S    M N S
1151    CTATCACCTT GACCGCTGAA GTCATGTCCT ACATTCACTC TATGAACTCC
        GATAGTGGAA CTGGCGACTT CAGTACAGGA TGTAAGTGAG ATACTTGAGG
```

FIG.2B

```
            S   I   L   E   N   W   N   F   G   V   P   P   P   P   T   T   S
1201    TCTATCTTGG AAAACTGGAA CTTCGGTGTT CCACCACCAC CAACCACCTC
        AGATAGAACC TTTTGACCTT GAAGCCACAA GGTGGTGGTG GTTGGTGGAG
            L   V   D   T   Y   R   F   V   Q   S   V   A   V   T   C   Q   K
1251    CTTGGTTGAC ACTTACAGAT TCGTCCAATC TGTCGCTGTC ACTTGTCAAA
        GAACCAACTG TGAATGTCTA AGCAGGTTAG ACAGCGACAG TGAACAGTTT
            D   T   T   P   P   E   K   Q   D   P   Y   D   K   L   K   F
1301    AGGACACCAC TCCACCAGAA AAGCAAGACC CATACGACAA GTTGAAGTTC
        TCCTGTGGTG AGGTGGTCTT TTCGTTCTGG GTATGCTGTT CAACTTCAAG
            W   T   V   D   L   K   E   K   F   S   S   D   L   D   Q   Y   P
1351    TGGACTGTTG ACTTGAAGGA AAAGTTCTCT TCCGACTTGG ACCAATACCC
        ACCTGACAAC TGAACTTCCT TTTCAAGAGA AGGCTGAACC TGGTTATGGG
            L   G   R   K   F   L   V   Q   A   G   L   R   R   R   P   T   I
1401    ATTGGGTAGA AAGTTCTTGG TTCAAGCTGG TTTGAGACGT AGACCAACTA
        TAACCCATCT TTCAAGAACC AAGTTCGACC AAACTCTGCA TCTGGTTGAT
            G   P   R   K   R   P   A   A   S   T   S   T   A   S   R   P
1451    TCGGTCCACG TAAGAGACCA GCTGCTTCCA CTTCCACTGC TTCTAGACCA
        AGCCAGGTGC ATTCTCTGGT CGACGAAGGT GAAGGTGACG AAGATCTGGT
            A   K   R   V   R   I   R   S   K   K   *   (SEQ ID NO:2)
1501    GCTAAGCGTG TCAGAATCAG ATCCAAGAAG TAA (SEQ ID NO:1)
        CGATTCGCAC AGTCTTAGTC TAGGTTCTTC ATT (SEQ ID NO:8)
```

FIG.2C

NORTHERN BLOT ANALYSIS OF HPV 45 L1 R.

ELISA ASSAY

| L1 CONSTRUCT | ng VLP/mcg TOTAL PROTEIN | FOLD INCREASE OVER WILD-TYPE |
|---|---|---|
| 45 L1 WILD-TYPE | 5 ng VLP/mcg TOTAL PROTEIN | na |
| 45 L1 ISOLATE #4 | 12 ng VLP/mcg TOTAL PROTEIN | 2.4 |
| 45 L1 R ISOLATE #11 | 10 ng VLP/mcg TOTAL PROTEIN | 2.0 |

FIG.5

TRANSMISSION EM OF VLPs COMPOSED OF HPV 45 L1 R PROTEIN MOLECULES.

SEQUENCE LISTING

```
<160> NUMBER OF SEQ ID NOS: 8

<210> SEQ ID NO 1
<211> LENGTH: 1533
<212> TYPE: DNA
<213> ORGANISM: Artificial Sequence
<220> FEATURE:
<223> OTHER INFORMATION: HPV45 L1R

<400> SEQUENCE: 1
atggctttgt ggagaccatc tgactctact gtctacttgc caccaccatc tgtcgctaga      60
gtcgtcaaca ctgacgacta cgtctccaga acctccatct tctaccacgc tggttcttcc     120
agattgttga ctgtcggtaa cccatacttc agagtcgtcc catccggtgc tggtaacaag     180
caagctgttc aaaggtctc tgcttaccaa tacagagtct tcagagtcgc tttgccagac     240
ccaaacaagt tcggtttgcc agactctact atctacaacc cagaaactca aagattggtc     300
tgggcatgcg tcggtatgga aatcggtaga ggtcaaccat tgggtatcgg tttgtctggt     360
cacccattct acaacaagtt ggacgacacc gaatccgctc acgctgctac tgctgtcatc     420
actcaagacg tcagagacaa cgtctctgtc gactacaagc aaacccaatt gtgtatcttg     480
ggttgtgtcc cagctatcgg tgaacactgg gctaagggta ccttgtgtaa gccagctcaa     540
ttgcaaccag tgactgtcc accattggaa ttgaagaaca ctatcatcga agacggtgac     600
atggttgaca ctggttacgg tgctatggac ttctccaccc tgcaggacac taagtgtgaa     660
gttccattgg acatctgtca atctatctgt aagtacccag actacttgca aatgtccgct     720
gacccatacg tgactctat gttcttctgt ttgagaagag aacaattgtt cgctagacac     780
ttctggaaca gagctggtgt catgggtgac actgttccaa ctgacttgta catcaagggt     840
acctctgcta acatgagaga aactccaggt tcctgtgtct actctccatc tccatctggt     900
tctatcacta cttccgactc tcaattgttc aacaagccat actggttgca caaggctcaa     960
ggtcacaaca acgtatctg ttggcacaac caattgttcg tcaccgtcgt tgacactacc    1020
agatctacta acttgacctt gtgtgcttct actcaaaaacc cagttccaaa cacttacgac    1080
```

```
ccaaccaagt tcaagcacta ctccagacac gtcgaggaat acgacttgca attcatcttc    1140
caattgtgta ctatcacctt gaccgctgaa gtcatgtcct acattcactc tatgaactcc    1200
tctatcttgg aaaactggaa cttcggtgtt ccaccaccac caaccacctc cttggttgac    1260
acttacagat tcgtccaatc tgtcgctgtc acttgtcaaa aggacaccac tccaccagaa    1320
aagcaagacc catacgacaa gttgaagttc tggactgttg acttgaagga aaagttctct    1380
tccgacttgg accaataccc attgggtaga agttcttgg ttcaagctgg tttgagacgt    1440
agaccaacta tcggtccacg taagagacca gctgcttcca cttccactgc ttctagacca    1500
gctaagcgtg tcagaatcag atccaagaag taa    1533
```

<210> SEQ ID NO 2
<211> LENGTH: 510
<212> TYPE: PRT
<213> ORGANISM: Human Papillomavirus Type 45

<400> SEQUENCE: 2

```
Met Ala Leu Trp Arg Pro Ser Asp Ser Thr Val Tyr Leu Pro Pro Pro
 1               5                  10                  15

Ser Val Ala Arg Val Val Asn Thr Asp Asp Tyr Val Ser Arg Thr Ser
            20                  25                  30

Ile Phe Tyr His Ala Gly Ser Ser Arg Leu Leu Thr Val Gly Asn Pro
        35                  40                  45

Tyr Phe Arg Val Val Pro Ser Gly Ala Gly Asn Lys Gln Ala Val Pro
    50                  55                  60

Lys Val Ser Ala Tyr Gln Tyr Arg Val Phe Arg Val Ala Leu Pro Asp
65                  70                  75                  80

Pro Asn Lys Phe Gly Leu Pro Asp Ser Thr Ile Tyr Asn Pro Glu Thr
                85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
        115                 120                 125

Asp Thr Glu Ser Ala His Ala Ala Thr Ala Val Ile Thr Gln Asp Val
    130                 135                 140

Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
                165                 170                 175

Lys Pro Ala Gln Leu Gln Pro Gly Asp Cys Pro Pro Leu Glu Leu Lys
            180                 185                 190

Asn Thr Ile Ile Glu Asp Gly Asp Met Val Asp Thr Gly Tyr Gly Ala
        195                 200                 205

Met Asp Phe Ser Thr Leu Gln Asp Thr Lys Cys Glu Val Pro Leu Asp
    210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
        275                 280                 285
```

-continued

```
Pro Gly Ser Cys Val Tyr Ser Pro Ser Gly Ser Ile Thr Thr
    290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
        355                 360                 365

Arg His Val Glu Glu Tyr Asp Leu Gln Phe Ile Phe Gln Leu Cys Thr
    370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Glu Lys Gln Asp Pro Tyr Asp Lys Leu
        435                 440                 445

Lys Phe Trp Thr Val Asp Leu Lys Glu Lys Phe Ser Ser Asp Leu Asp
450                 455                 460

Gln Tyr Pro Leu Gly Arg Lys Phe Leu Val Gln Ala Gly Leu Arg Arg
465                 470                 475                 480

Arg Pro Thr Ile Gly Pro Arg Lys Arg Pro Ala Ala Ser Thr Ser Thr
                485                 490                 495

Ala Ser Arg Pro Ala Lys Arg Val Arg Ile Arg Ser Lys Lys
        500                 505                 510

<210> SEQ ID NO 3
<211> LENGTH: 1533
<212> TYPE: DNA
<213> ORGANISM: Human Papillomavirus Type 45

<400> SEQUENCE: 3
atggctttgt ggcggcctag tgacagtacg gtatatcttc caccaccttc tgtggccaga      60
gttgtcaaca ctgatgatta tgtgtctcgc acaagcatat tttaccatgc aggcagttcc     120
cgattattaa ctgtaggcaa tccatatttt agggttgtac ctagtggtgc aggtaataaa     180
caggctgttc ctaaggtatc cgcatatcag tatagggtgt tagagtagc tttgcccgat      240 cctaataaat ttggattacc tgattctact atatataatc ctgaaacaca acgtttggtt     300
tgggcatgtg taggtatgga aattggtcgt gggcagcctt aggtattgg cctaagtggc     360 catccatttt ataataaatt ggatgataca gaaagtgctc atgcagctac agctgttatt     420
acgcaggatg ttagggataa tgtgtcagtt gattataagc aaacacagct gtgtatttta     480
ggttgtgtac ctgctattgg tgagcactgg gccagggca cactttgtaa acctgcacaa     540
ttgcaacctg tgactgtcc tcctttggaa cttaaaaaca ccattattga ggatggtgat     600
atggtggata caggttatgg ggcaatggat tttagtacat tgcaggatac aaagtgcgag     660
gttccattag acatttgtca atccatctgt aaatatccag attatttgca aatgtctgct     720 gatcctatg gggattctat gttttttttgc ctacgccgtg aacaactgtt tgcaagacat     780
ttttggaata gggcaggtgt tatgggtgac acagtaccta cagacctata tattaaaggc     840
actagcgcta atatgcgtga aacccctggc agttgtgtgt attccccttc tcccagtggc     900
```

```
tctattacta cttctgattc tcaattattt aataagccat attggttaca taaggcccag    960
ggccataaca atggtatttg ttggcataat cagttgtttg ttactgtagt ggacactacc   1020
cgcagtacta atttaacatt atgtgcctct acacaaaatc ctgtgccaaa tacatatgat   1080
cctactaagt ttaagcacta tagtagacat gtggaggaat atgatttaca gtttattttt   1140
cagttgtgca ctattacttt aactgcagag gttatgtcat atatccatag tatgaatagt   1200
agtatattgg aaaattggaa ttttggtgta cctccaccac ctactacaag tttagtggat   1260
acatatcgtt ttgtgcaatc agttgctgtt acctgtcaaa aggatactac acctccagaa   1320
aagcaggatc catatgataa attaaagttt tggactgttg acctaaagga aaaattttcc   1380
tccgatttgg atcaatatcc ccttggtcga aagttttttag ttcaggctgg gttacgtcgt   1440
aggcctacca taggacctcg taagcgtcct gctgcttcca cgtctactgc atctaggcct   1500
gccaaacgtg tacgtatacg tagtaaaaaa taa                                1533

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
ccaccaccac ctatataggt attc                                            24

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
caaacataca tatatgtgct aaca                                            24

<210> SEQ ID NO 6
<211> LENGTH: 44
<212> TYPE: DNA
<213> ORGANISM: Artificial Sequence
<220> FEATURE:
<223> OTHER INFORMATION: PCR Primer

<400> SEQUENCE: 6
ctcagatctc acaaaacaaa atggctttgt ggcggcctag tgac                      44

<210> SEQ ID NO 7
<211> LENGTH: 35
<212> TYPE: DNA
<213> ORGANISM: Artificial Sequence
<220> FEATURE:
<223> OTHER INFORMATION: PCR Primer

<400> SEQUENCE: 7
gacagatctt attttttact acgtatacgt acacg                                35

<210> SEQ ID NO 8
<211> LENGTH: 1533
<212> TYPE: DNA
<213> ORGANISM: Artificial Sequence
<220> FEATURE:
<223> OTHER INFORMATION: HPV45 L1R - Antisense
```

-continued

```
<400> SEQUENCE: 8
taccgaaaca cctctggtag actgagatga cagatgaacg gtggtggtag acagcgatct        60
cagcagttgt gactgctgat gcagaggtct tggaggtaga agatggtgcg accaagaagg       120
tctaacaact gacagccatt gggtatgaag tctcagcagg gtaggccacg accattgttc       180
gttcgacaag gtttccagag acgaatggtt atgtctcaga agtctcagcg aaacggtctg       240
ggtttgttca agccaaacgg tctgagatga tagatgttgg gtctttgagt ttctaaccag       300
acccgtacgc agccatacct ttagccatct ccagttggta acccatagcc aaacagacca       360
gtgggtaaga tgttgttcaa cctgctgtgg cttaggcgag tgcgacgatg acgacagtag       420
tgagttctgc agtctctgtt gcagagacag ctgatgttcg tttgggttaa cacatagaac       480
ccaacacagg gtcgatagcc acttgtgacc cgattcccat ggaacacatt cggtcgagtt       540
aacgttggtc cactgacagg tggtaacctt aacttcttgt gatagtagct tctgccactg       600
taccaactgt gaccaatgcc acgatacctg aagaggtggg acgtcctgtg attcacactt       660
caaggtaacc tgtagacagt tagatagaca ttcatgggtc tgatgaacgt ttacaggcga       720
ctgggtatgc cactgagata caagaagaca aactcttctc ttgttaacaa gcgatctgtg       780
aagaccttgt ctcgaccaca gtacccactg tgacaaggtt gactgaacat gtagttccca       840
tggagacgat tgtactctct ttgaggtcca aggacacaga tgagaggtag aggtagacca       900
agatagtgat gaaggctgag agttaacaag ttgttcggta tgaccaacgt gttccgagtt       960
ccagtgttgt tgccatagac aaccgtgttg gttaacaagc agtggcagca actgtgatgg      1020
tctagatgat tgaactggaa cacacgaaga tgagttttgg gtcaaggttt gtgaatgctg      1080
ggttggttca agttcgtgat gaggtctgtg cagctcctta tgctgaacgt taagtagaag      1140
gttaacacat gatagtggaa ctggcgactt cagtacagga tgtaagtgag atacttgagg      1200
agatagaacc ttttgaccct gaagccacaa ggtggtggtg gttggtggag gaaccaactg      1260
tgaatgtcta agcaggttag acagcgacag tgaacagttt tcctgtggtg aggtggtctt      1320
ttcgttctgg gtatgctgtt caacttcaag acctgacaac tgaacttcct tttcaagaga      1380
aggctgaacc tggttatggg taacccatct ttcaagaacc aagttcgacc aaactctgca      1440
tctggttgat agccaggtgc attctctggt cgacgaaggt gaaggtgacg aagatctggt      1500
cgattcgcac agtcttagtc taggttcttc att                                   1533
```

OPTIMIZED EXPRESSION OF HPV 45 L1 IN YEAST

CROSS-REFERENCE TO RELATED APPLICATIONS

This application is a §371 National Stage Application of PCT/US2004/031326, international filing date of Sep. 24, 2004, which claims the benefit of U.S. Provisional Application No. 60/506,812, filed Sep. 29, 2003, now expired.

FIELD OF THE INVENTION

The present invention relates generally to the therapy of human papillomavirus (HPV). More specifically, the present invention relates to synthetic polynucleotides encoding HPV45 L1 protein, and to recombinant vectors and hosts comprising said polynucleotides. This invention also relates to HPV45 virus-like particles (VLPs), wherein the VLPs are produced by expressing recombinant HPV 45 L1 or L1+L2 in yeast cells and to their use in vaccines and pharmaceutical compositions for preventing and treating HPV.

BACKGROUND OF THE INVENTION

There are more than 80 types of human papillomavirus (HPV), many of which have been associated with a wide variety of biological phenotypes, from benign proliferative warts to malignant carcinomas (for review, see McMurray et al., *Int. J. Exp. Pathol.* 82(1): 15-33 (2001)). HPV6 and HPV11 are the types most commonly associated with benign warts and/or nonmalignant condyloma acuminata of the genital or respiratory mucosa. HPV16 and HPV18 are the high-risk types most frequently associated with in situ and invasive carcinomas of the cervix, vagina, vulva and anal canal. More than 90% of cervical carcinomas are associated with infections of HPV16, HPV18 or the less prevalent oncogenic types HPV31, -33, -45, -52 and -58 (Schiffman et al., *J. Natl. Cancer Inst.* 85(12): 958-64 (1993)). The observation that HPV DNA is detected in more than 90% of cervical cancers provides strong epidemiological evidence that HPVs cause cervical carcinoma (see Bosch et al., *J. Natl. Cancer Inst.* 87(11): 796-802 (1995)).

Papillomaviruses are small (50-60 nm), nonenveloped, icosahedral DNA viruses that encode up to eight early and two late genes. The open reading frames (ORFs) of the viral genomes are designated E1 to E7, and L1 and L2, where "E" denotes early and "L" denotes late. L1 and L2 code for virus capsid proteins, while the E genes are associated with functions such as viral replication and cellular transformation.

The L1 protein is the major capsid protein and has a molecular weight of 55-60 kDa. The L2 protein is the minor capsid protein. Immunological data suggest that most of the L2 protein is internal to the L1 protein in the viral capsid. Both the L1 and L2 proteins are highly conserved among different papillomaviruses.

Expression of the L1 protein or a combination of the L1 and L2 proteins in yeast, insect cells, mammalian cells or bacteria leads to self-assembly of virus-like particles (VLPs) (for review, see Schiller and Roden, in *Papillomavirus Reviews: Current Research on Papillomaviruses;* Lacey, ed. Leeds, UK: Leeds Medical Information, pp 101-12 (1996)). VLPs are morphologically similar to authentic virions and are capable of inducing high titres of neutralizing antibodies upon administration into an animal. Because VLPs do not contain the potentially oncogenic viral genome, they present a safe alternative to the use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

HPV vaccine development and commercialization have been hindered by difficulties associated with obtaining high expression levels of exogenous genes in successfully transformed host organisms, limiting the production of purified protein. Therefore, despite the identification of wild-type nucleotide sequences encoding HPV L1 proteins such as HPV45 L1 protein, it would be highly desirable to develop a readily renewable source of crude HPV L1 protein that utilizes HPV45 L1-encoding nucleotide sequences that are optimized for expression in the intended host cell. Additionally, it would be useful to produce large quantities of HPV45 L1 VLPs having the immunity-conferring properties of the native proteins for use in vaccine development.

SUMMARY OF THE INVENTION

The present invention relates to compositions and methods to elicit or enhance immunity to the protein products expressed by HPV45 L1 genes, which have been associated with cervical cancer. Specifically, the present invention provides polynucleotides encoding HPV45 L1 protein, wherein the polynucleotides have been codon-op zed for high level expression in a yeast cell. The present invention further provides HPV45 virus-like particles (VLPs), wherein said VLPs are produced by expressing recombinant HPV45 L1 or L1+L2 in yeast cells and discloses use of HPV45 VLPs in pharmaceutical compositions and vaccines for the prevention and/or treatment of HPV-associated cancer.

The present invention relates to synthetic DNA molecules encoding the HPV45 L1 protein. The codons of the synthetic molecules are designed so as to use the codons preferred by a yeast cell. The synthetic molecules may be used as a source of HPV45 L1 protein, which may self-assemble into VLPs. Said VLPs may be used in a VLP-based vaccine.

An exemplary embodiment of the present invention comprises a synthetic nucleic acid molecule which encodes the HPV45 L1 protein as set forth in SEQ ID NO:2, said nucleic acid molecule comprising a sequence of nucleotides as set forth in SEQ ID NO:1.

Also provided are recombinant vectors and recombinant host cells, both prokaryotic and eukaryotic, which contain the nucleic acid molecules disclosed throughout this specification.

The present invention also relates to a process for expressing an HPV45 L1 protein in a recombinant host cell, comprising: (a) introducing a vector comprising a nucleic acid encoding an HPV45 L1 protein into a yeast host cell; and (b) culturing the yeast host cell under conditions which allow expression of said HPV45 L1 protein.

The present invention further relates to a process for expressing an HPV45 L1 protein in a recombinant host cell, comprising: (a) introducing a vector comprising a nucleic acid encoding an HPV45 L1 protein into a yeast host cell; wherein the nucleic acid molecule is codon-optimized for optimal expression in the yeast host cell and; (b) culturing the yeast host cell under conditions which allow expression of said HPV45 L1 protein.

In preferred embodiments, the nucleic acid comprises a sequence of nucleotides as set forth in SEQ ID NO:1 (45 L1 R sequence).

This invention also relates to HPV45 virus-like particles (VLPs) which are produced in yeast cells, methods of producing HPV45 VLPs, and methods of using HPV45 VLPs.

In a preferred embodiment of the invention, the yeast is selected from the group consisting of: *Saccharomyces cerevisiae*, *Hansenula polymorpha*, *Pichia pastoris*, *Kluyveromyces fragilis*, *Kluyveronzyces lactis*, and *Schizosaccharomyces pombe*.

Another aspect of this invention is an HPV45 VLP, wherein the VLP is produced by recombinant expression of HPV45 L1 or HPV45 L1+L2 in a yeast cell.

Yet another aspect of this invention is an HPV45 VLP which comprises an HPV45 L1 protein encoded by a codon-optimized HPV45 L1 gene. In an exemplary embodiment of this aspect of the invention, the codon-optimized HPV45 L1 gene comprises a sequence of nucleotides as set forth in SEQ ID NO:1.

This invention also provides a method for inducing an immune response in an animal comprising administering HPV45 virus-like particles to the animal. In a preferred embodiment, the HPV45 VLPs are produced by a codon-optimized gene.

Yet another aspect of this invention is a method of preventing or treating HPV-associated cervical cancer comprising administering to a mammal a vaccine comprising HPV45 VLPs. In a preferred embodiment of this aspect of the invention, the HPV45 VLPs are produced in yeast.

This invention also relates to a vaccine comprising HPV45 virus-like particles (VLPs).

In an alternative embodiment of this aspect of the invention, the vaccine further comprises VLPs of at least one additional HPV type. The at least one additional HPV type may be any HPV type of interest, including any HPV type described in the art or those subsequently identified. In a preferred embodiment, the HPV type is a type that is associated with a clinical phenotype such as warts or cervical cancer. In a further preferred embodiment, the at least one additional HPV type is selected from the group consisting of: HPV6, HPV11, HPV16, HPV18, HPV31, HPV33, HPV35, HPV39, HPV51, HPV52, HPV55, HPV56, HPV58, HPV59, and HPV68.

This invention also relates to pharmaceutical compositions comprising HPV 45 virus-like particles. Further, this invention relates to pharmaceutical compositions comprising HPV45 VLPs and VLPs of at least one additional HPV type. In a preferred embodiment, the at least one additional HPV type is selected from the group consisting of: HPV6, HPV11, HPV16, HPV18, HPV31, HPV33, HPV35, HPV39, HPV51, HPV52, HPV55, HPV56, HPV58, HPV59, and HPV68.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or "upstream activating sequences" or inhibiting sequences termed "silencers".

The term "vector" refers to some means by which DNA fragments can be introduced into a host organism or host tissue. There are various types of vectors including plasmids, viruses (including adenovirus), bacteriophages and cosmids.

The designation "45 L1 wild-type sequence" refers to the HPV45 L1 DNA sequence disclosed herein as SEQ ID NO:3 (45 L1 wt). Although the HPV 45 L1 wild-type DNA sequence has been described previously, it is not uncommon to find minor sequence variations between DNAs obtained from clinical isolates. Therefore, a representative 45 L1 wild-type DNA sequence was isolated from clinical samples previously shown to contain HPV 45 DNA (see EXAMPLE 1). The 45 L1 wild-type sequence was used as a reference sequence to compare the codon-optimized 45 L1 sequences disclosed herein (see FIG. 1).

The designation "HPV 45 L1 R" or "45 L1 R" refers to an exemplary synthetic HPV45 L1 nucleotide sequence (SEQ ID NO:1), disclosed herein, wherein the sequence was rebuilt so that it comprises codons that are preferred for high-level expression by a yeast cell.

The term "effective amount" means sufficient vaccine composition is introduced to produce the adequate levels of the polypeptide, so that an immune response results. One skilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

"VLP" or "VLPs" mean(s) virus-like particle or virus-like particles.

"Synthetic" means that the HPV45 L1 gene was created so that it contains a sequence of nucleotides that is not the same as the sequence of nucleotides present in the designated naturally occurring wild-type HPV45 L1 gene (45 L1 wt, SEQ ID NO:3). As stated above, synthetic molecules are provided herein comprising a sequence of nucleotides comprising codons that are preferred for expression by yeast cells. The synthetic molecules provided herein encode the same amino acid sequence as the wild-type HPV45 L1 gene (SEQ ID NO:2).

BRIEF DESCRIPTION OF THE DRAWINGS

FIG. 1 is a DNA sequence alignment showing nucleotides that were altered in the synthetic HPV45 L1 gene of the present invention (SEQ ID NO:1, indicated as "45 L1 R") (See EXAMPLE 2). The reference sequence is the 45 L1 wild-type sequence (SEQ ID NO:3, indicated as "45 L1 wt"; see EXAMPLE 1). Altered nucleotides are indicated at their corresponding location. Nucleotide number is contained within the parentheses. Identical nucleotides in the 45 L1 rebuilt sequence are indicated with dots.

FIG. 2 shows the rebuilt synthetic HPV 45 L1 nucleotide and single-code amino acid sequence. Nucleotide number is indicated to the left.

FIG. 5 shows a portion of the data from two ELISA experiments in ng VLP/µg total protein (see EXAMPLE 7). A comparison between 45 L1 wt and two separate clones of 45 L1 R, is shown. Rebuilt HPV 45 L1 VLP expression was approximately 2 fold higher than the 45 L1 wt.

DETAILED DESCRIPTION OF THE INVENTION

Figure 3:
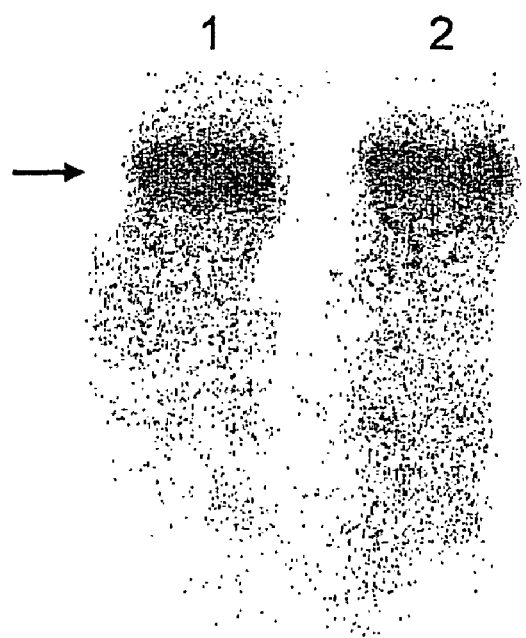
FIG. 3 shows a Northern blot probed specifically for HPV 45 L1 RNA under high stringency conditions (see EXAMPLE 4). Lane (1) contains 5 μg of HPV 45 L1 R RNA and lane (2) contains 10 μg of HPV 45 L1 R RNA. A single full-length RNA transcript is apparent on the blot. Arrow on left indicates the predicted position of a full length HPV 45 L1 transcript.

The majority of cervical carcinomas are associated with infections of specific oncogenic types of human papillomavirus (HPV). The present invention relates to compositions and methods to elicit or enhance immunity to the protein products expressed by genes of oncogenic HPV types. Specifically, the present invention provides polynucleotides encoding HPV45 L1 protein, which self-assemble into HPV45 virus-like particles (VLPs) and discloses use of said polynucleotides and VLPs in pharmaceutical compositions and vaccines for the prevention and/or treatment of HPV-associated cancer.

The wild-type HPV45 L1 nucleotide sequence has been reported (Genbank Accession # NC_001590; see also Delius and Hofmann, Curr. Top. Microbiol. Immunol. 186: 13-31 (1994)). The present invention provides synthetic DNA molecules encoding the HPV45 L1 protein. The synthetic molecules of the present invention comprise a sequence of codons, wherein at least a portion of the codons have been altered to use the codons preferred by a yeast cell for high-level expression. The synthetic molecules may be used as a coding sequence for expression of HPV45 L1 protein, which may self-assemble into VLPs. Said VLPs may be used in a VLP-based vaccine to provide effective immunoprophylaxis against papillomavirus infection through neutralizing antibody and cell-mediated immunity.

Expression of HPV VLPs in yeast cells offers the advantages of being cost-effective and easily adapted to large-scale growth in fermenters. However, many HPV L1 proteins, including HPV45 L1 are expressed at levels in yeast cells which are lower than what is desirable for commercial scale-up.

Accordingly, the present invention relates to HPV45 L1 gene sequences that are "optimized" for high level expression in a yeast cellular environment.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon use frequencies for microorganisms has revealed endogenous DNA of E. coli most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an E. coli host will depend to some extent on the frequency of codon use. For example, it is likely that a gene rich in TTA codons will be poorly expressed in E. coli, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant protein expression. Thus, one aspect of this invention is an HPV45 L1 gene that is codon-optimized for high-level expression in a yeast cell. In a preferred embodiment of this invention, it has been found that the use of alternative codons encoding the same protein sequence may remove the constraints on expression of HPV45 L1 proteins by yeast cells.

In accordance with this invention, HPV45 L1 gene segments were converted to sequences having identical translated sequences but with alternative codon usage as described by Sharp and Cowe (Synonymous Codon Usage in Saccharomyces cerevisiae. Yeast 7: 657-678 (1991)), which is hereby incorporated by reference. The methodology generally consists of identifying codons in the wild-type sequence that are not commonly associated with highly expressed yeast genes and replacing them with optimal codons for high expression in yeast cells. The new gene sequence is then inspected for undesired sequences generated by these codon replacements (e.g., "ATTTA" sequences, inadvertent creation of intron splice recognition sites, unwanted restriction enzyme sites, high GC content, presence of transcription termination signals that are recognized by yeast, etc.). Undesirable sequences are eliminated by substitution of the existing codons with different codons coding for the same amino acid. The synthetic gene segments are then tested for improved expression.

The methods described above were used to create synthetic gene segments for HPV45 L1, resulting in a gene comprising codons optimized for high level expression in a yeast cellular environment. While the above procedure provides a summary of our methodology for designing codon-optimized genes for use in HPV vaccines, it is understood by one skilled in the art that similar vaccine efficacy or increased expression of genes may be achieved by minor variations in the procedure or by minor variations in the sequence.

Accordingly, the present invention relates to a synthetic polynucleotide comprising a sequence of nucleotides encoding an HPV45 L1 protein, or a biologically active fragment or mutant form of an HPV45 L1 protein, the polynucleotide sequence comprising codons optimized for expression in a yeast host cell. Said mutant forms of the HPV45 L1 protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the HPV45 L1 protein as set forth in SEQ ID NO:2. The synthetic polynucleotides of the present invention encode mRNA molecules that express a functional HPV45 L1 protein so as to be useful in the development of a therapeutic or prophylactic HPV vaccine.

One aspect of this invention is a codon-optimized nucleic acid molecule which encodes the HPV45 L1 protein as set forth in SEQ ID NO:2, said nucleic acid molecule comprising a sequence of nucleotides as set forth in SEQ ID NO:1.

The present invention also relates to recombinant vectors and recombinant host cells, both prokaryotic and eukaryotic, which contain the nucleic acid molecules disclosed throughout this specification.

The synthetic HPV45 DNA or fragments thereof constructed through the methods described herein may be recombinantly expressed by molecular cloning into an expression vector containing a suitable promoter and other appropriate transcription regulatory elements, and transferred into prokaryotic or eukaryotic host cells to produce recombinant HPV45 L1. Techniques for such manipulations are fully described by Sambrook et al. (*Molecular Cloning: A Laboratory Manual;* Cold Spring Harbor Laboratory, Cold Spring Harbor, N.Y., (1989); *Current Protocols in Molecular Biology*, Ausubel et al., Green Pub. Associates and Wiley-Interscience, New York (1988); *Yeast Genetics: A Laboratory Course Manual*, Rose et al., Cold Spring Harbor Laboratory, Cold Spring Harbor, N.Y., (1990)), which are hereby incorporated by reference in their entirety.

Thus, the present invention relates to a process for expressing an HPV45 L1 protein in a recombinant host cell, comprising: (a) introducing a vector comprising a nucleic acid encoding an HPV45 L1 protein into a yeast host cell; and (b) culturing the yeast host cell under conditions which allow expression of said HPV45 L1 protein.

The present invention further relates to a process for expressing an HPV45 L1 protein in a recombinant host cell, comprising: (a) introducing a vector comprising a nucleic acid encoding an HPV45 L1 protein into a yeast host cell; wherein the nucleic acid molecule is codon-optimized for optimal expression in the yeast host cell and; (b) culturing the yeast host cell under conditions which allow expression of said HPV45 L1 protein.

This invention further relates to a process for expressing an HPV45 L1 protein in a recombinant host cell, comprising: (a) introducing a vector comprising a nucleic acid as set forth in SEQ ID NO:1 into a yeast host cell; and, (b) culturing the yeast host cell under conditions which allow expression of said HPV45 L1 protein.

The synthetic genes of the present invention can be assembled into an expression cassette that comprises sequences designed to provide efficient expression of the HPV45 L1 protein in the host cell. The cassette preferably contains the synthetic gene, with related transcriptional and translations control sequences operatively linked to it, such as a promoter, and termination sequences. In a preferred embodiment, the promoter is the *S. cerevisiae* GAL1 promoter, although those skilled in the art will recognize that any of a number of other known yeast promoters such as the GAL10, GAL7, ADH1, TDH3, or PGK promoters, or other eukaryotic gene promoters may be used. A preferred transcriptional terminator is the *S. cerevisiae* ADH1 terminator, although other known transcriptional terminators may also be used. The combination of GAL1 promoter—ADH1 terminator is particularly preferred.

Another aspect of this invention is an HPV45 virus-like particle (VLP) produced by recombinantly expressing the HPV45 L1 or L1+L2 genes in a yeast cell, methods of producing HPV45 VLPs, and methods of using HPV45 VLPs. VLPs can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses;* Lacey, ed. Leeds, UK: Leeds Medical Information, pp 101-12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Biophys. J.* 60(6): 1445-56 (1991)).

VLPs are morphologically similar to authentic virions and are capable of inducing high titres of neutralizing antibodies upon administration into an animal. Immunization of rabbits (Breitburd et al., *J. Virol.* 69(6): 3959-63 (1995)) and dogs (Suzich et al., *Proc. Natl. Acad. Sci. USA* 92(25): 57 (1995)) with VLPs was shown to both induce neutralizing antibodies and protect against experimental papillomavirus infection. However, because the VLPs do not contain the potentially oncogenic viral genome and can self-assemble when expressed from a single gene, they present a safe alternative to the use of live virus in HPV vaccine development (for review, see Schiller and Hidesheim, *J. Clin. Virol.* 19: 67-74 (2000)).

Marais and colleagues (*J. Med. Virol.* 60: 331-336 (2000)) disclose HPV 45 VLPs, which were produced in insect cells from an HPV45 L1 gene expressed from baculovirus. Expression of VLPs in insect cells is not advantageous for vaccine development because of the high associated costs. Additionally, it is often difficult to scale-up expression of HPV L1 genes in insect cell culture to the large volumes necessary for commercial product development. HPV 45 VLPs produced in yeast cells have not been described. Expression of HPV VLPs in yeast cells offers the advantages of being cost-effective and easily adapted to large-scale growth in fermenters. In addition, the yeast genome can be readily altered to ensure selection of recombinant, transformed yeast with increased growth and expression potential.

Thus, the present invention relates to virus-like particles comprised of recombinant L1 protein or recombinant L1+L2 proteins of HPV45, wherein the recombinant protein is expressed in a yeast cell.

In a preferred embodiment of the invention, the HPV45 VLPs are produced by expressing HPV 45 L1 or HPV 45 L1+L2 in a yeast selected from the group consisting of: *Saccharomyces cerevisiae, Hansenula polymorpha, Pichia pastoris, Kluyveromyces fragilis, Kluyveromyces lactis*, and *Schizosaccharomyces pombe*.

Another aspect of this invention is an HPV45 VLP which comprises an HPV45 L1 protein produced by expressing a codon-optimized HPV45 L1 gene. In a preferred embodiment of this aspect of the invention, the codon-optimized HPV45 L1 gene comprises a sequence of nucleotides as set forth in SEQ ID NO:1.

Yet another aspect of this invention is a method of producing HPV45 VLPs, comprising: (a) transforming yeast with a recombinant DNA molecule encoding HPV45 L1 protein or HPV45 L1+L2 proteins; (b) cultivating the transformed yeast under conditions that permit expression of the recombinant DNA molecule to produce the recombinant HPV45 protein; and (c) isolating the recombinant HPV45 protein to produce HPV45 VLPs.

In a preferred embodiment of this aspect of the invention, the yeast is transformed with a codon-optimized HPV45 L1 gene to produce HPV45 VLPs. In a particularly preferred embodiment, the codon-optimized HPV45 L1 gene comprises a sequence of nucleotides as set forth in SEQ ID NO:1.

This invention also provides a method for inducing an immune response in an animal comprising administering HPV45 virus-like particles to the animal. In a preferred embodiment, the HPV45 VLPs are produced by a codon-optimized gene.

Yet another aspect of this invention is a method of preventing or treating HPV-associated cervical cancer comprising administering to a mammal a vaccine comprising HPV45 VLPs. In a preferred embodiment of this aspect of the invention, the HPV45 VLPs are produced in yeast.

This invention also relates to a vaccine comprising HPV45 virus-like particles (VLPs).

In an alternative embodiment of this aspect of the invention, the vaccine further comprises VLPs of at least one additional HPV type. In a preferred embodiment, the at least one additional HPV type is selected from the group consisting of: HPV6, HPV11, HPV16, HPV18, HPV31, HPV33, HPV35, HPV39, HPV51, HPV52, HPV55, HPV56, HPV58, HPV59, and HPV68.

In a preferred embodiment of this aspect of the invention, the vaccine further comprises HPV16 VLPs.

In another preferred embodiment of the invention, the vaccine further comprises HPV16 VLPs and HPV18 VLPs.

In yet another preferred embodiment of the invention, the vaccine further comprises HPV6 VLPs, HPV11 VLPs, HPV16 VLPs and HPV18 VLPs.

This invention also relates to pharmaceutical compositions comprising HPV 45 virus-like particles. Further, this invention relates to pharmaceutical compositions comprising HPV45 VLPs and VLPs of at least one additional HPV type. In a preferred embodiment, the at least one additional HPV type is selected from the group consisting of: HPV6, HPV11, HPV 16, HPV18, HPV31, HPV33, HPV35, HPV39, HPV51, HPV52, HPV55, HPV56, HPV58, HPV59, and HPV68.

Vaccine compositions of the present invention may be used alone at appropriate dosages defined by routine testing in order to obtain optimal inhibition of HPV45 infection while minimizing any potential toxicity. In addition, co-administration or sequential administration of other agents may be desirable.

The amount of virus-like particles to be introduced into a vaccine recipient will depend on the immunogenicity of the expressed gene product. In general, an immunologically or prophylactically effective dose of about 10 µg to 100 µg, and preferably about 20 µg to 60 µg of VLPs is administered directly into muscle tissue. Subcutaneous injection, intradermal introduction, impression though the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as alum or Merck aluminum adjuvant, concurrently with or subsequent to parenteral introduction of the vaccine of this invention is also advantageous.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Determination of a Representative HPV 45 L1 Sequence

The HPV 45 L1 sequence has been described previously (Genbank Accession # NC_001590; see Delius and Hofmann Curr. Top. Microbiol. Immunol. 186: 13-31 (1994)). It is not uncommon, however, to find minor sequence variations between DNAs obtained from clinical isolates. To determine a representative HPV45 L1 wild-type sequence, DNA was isolated from four clinical samples previously shown to contain HPV 45 DNA. HPV 45 L1 sequences were amplified in a polymerase chain reaction (PCR) using Taq DNA polymerase and the following primers: HPV 45 L1 F 5'-CCACCACCACCTATATAGGTATTC-3'(SEQ ID NO:4) and HPV45 L1 B 5'-C AAACATACATATATGT-GCTAACA-3'(SEQ ID NO:5). The amplified products were electrophoresed on agarose gels and visualized by ethidium bromide staining. The ~1500 bp L1 bands were excised and DNA purified using the QIA quick PCR purification kit (Qiagen, Hilden, Germany). The DNA was then ligated to a TA cloning vector (Invitrogen Corp., Carlsbad, Calif.), E. Coli was transformed with the ligation mixture and plated on LB agar with ampicillin plus IPTG and X-gal for blue/white colony selection. The plates were inverted and incubated for 16 hours at 37° C.

Colony PCR was performed on eight white colonies originating from each of the four clinical isolates that had been PCR amplified. HPV 45 L1 DNA was PCR-amplified using primers HPV 45 L1 F and HPV 45 L1 B. The specific PCR protocol consisted of 25 cycles of 15 seconds at 98° C. (denaturation), 30 seconds at 50° C. (annealing) and 2 minutes at 68° C. (extension). PCR products were visualized by ethidium bromide staining after agarose gel electrophoresis. Several colonies from each isolate contained L1 bands. The second colony from each isolate was cultured in LB medium with ampicillin, shaking at 37° C. for 16 hours. Minipreps were performed to extract plasmid DNA from the colonies.

DNA sequencing was performed on the plasmids containing amplified and cloned HPV 45 L1 DNA from the four clinical isolates. DNA and translated amino acid sequences were compared with one another and the Genbank HPV 45 L1 sequences. Sequence analysis of the four clinical isolates revealed that no sequence was identical to the Genbank sequence. The HPV 45 L1 plasmid from isolate #33 was chosen to be the representative 45 L1 wild-type (wt) sequence and is referred to herein as the "45 L1 wild-type sequence" (SEQ ID NO:3, see FIG. 1). This sequence contained a nine nucleotide, three amino acid, deletion which maintained the subsequent sequence reading frame, five point mutations resulting in five amino acids changes and eight additional silent point mutations. Amino acids 495-497 in the Genbank sequence are deleted in the 45 L1 wt. Genbank amino acids numbers 23 (S->N), 55 (N->S), 303 (I->T), 357 (S->N), and 356 (Q->H) represent the five amino acids changes (Genbank aa->45 L1 wt aa). The 8 silent mutations were distributed throughout the sequence. See FIG. 1.

The 45 L1 wild-type sequence was amplified using the LS-112 5'-CTCAGATCT CACAAAACAAAATG-GCTTTGTGGCGGCCTAGTGAC-3' (SEQ ID NO:6) and HPV45 L1 EAS 5'-GACAGATCTTATTTTTTACTACG-TATACGTACAC G-3' (SEQ ID NO:7) primers to add BglII extensions. PCR was performed using Vent polymerase. The PCR product was visualize by ethidium bromide staining of an agarose gel. The ~1500 bp band was excised and DNA purified using the QIAEX II gel extraction kit (Qiagen). The PCR product was then digested with BglII at 37° C. for 2 hours and purified using the QIA quick PCR purification kit. The BglII-digested HPV 45 L1 PCR product was ligated to BamHI-digested pGAL110 (described in Hofmann et al., *Virology* 209: 506-18 (1995)) and *E. coli* DH5 was transformed with the ligation mixture.

Colonies were screened by PCR for the HPV 45 L1 insert in the correct orientation. Sequence and orientation were confirmed by DNA sequencing. The selected clone was named pGAL110-HPV 45 L1 #6. This clone was digested with PstI, EcoRI and HindIII to determine the restriction fragment profile of the HPV 45 L1 gene within the pGAL110 vector. DNA fragments were electrophoresed on agarose gels. The resulting restriction fragment profile was visualized by ethidium bromide staining and viewed with UV light Maxiprep DNA was prepared. *Saccharomyces cerevisiae* cells were made competent by spheroplasting with Glusulase and transformed with pGAL110-HPV 45 L1 #6. The yeast transformation mixture was plated in Leu(–) sorbitol top-agar onto Leu(–) sorbitol plates and incubated inverted for 5-7 days at 30° C. Colonies were picked and streaked for clonal isolation on Leu(–) sorbitol plates. Isolated colonies were subsequently grown in 5 ml of 5 X Leu(–) Ade(–) sorbitol with 1.6% glucose and 4% galactose in rotating tube cultures at 30° C. to induce L1 transcription and protein expression.

EXAMPLE 2

Yeast Codon Optimization

Yeast-preferred codons have been described (Sharp, Paul M and Cowe, Elizabeth 1991 Synonymous Codon Usage in *Saccharomyces cerevisiae* YEAST 7: 657-678). Expression of the HPV 45 L1 wt protein was detectable; however, to obtain the increased expression necessary for commercial product development, the HPV 45 L1 gene was rebuilt utilizing yeast-preferred codons. Said rebuilt sequence would provide increased HPV45 L1 expression, which would be a significant advance over the wild-type for use in vaccine development. When the sequence was rebuilt utilizing yeast-optimized codon sequences, the nucleotide sequence of 45 L1 wt was altered at 392 positions to produce 45 L1 R (R=rebuild). The amino acid sequence, however, was not altered. The nucleotide (SEQ ID NO:1) and amino acid (SEQ ID NO:2) sequences of HPV 45 L1 R are shown in FIG. 2.

The strategy employed for the gene rebuild was to design long overlapping sense and antisense oligomers that span the gene, substituting nucleotides with yeast-preferred codon sequences while maintaining the original amino acid sequence. These oligomers were used in place of template DNA in a PCR reaction. Additional amplification primers were designed and used to amplify the rebuilt sequences from the template oligomers. Pfu DNA polymerase was used in the PCR of 25 cycles.

The optimal conditions for amplification were section-specific, however most employed a program resembling 94° C. for 5 minutes (denaturing) followed by 25 cycles of 95° C. for 30 sec (denature), 55-50° C. for 30 sec (anneal), and 72° C. for 1.5 minute (extension), followed by a 7 minute final extension at 72° C. and 4° C. hold. PCR products were examined by agarose gel electrophoresis. Bands of the appropriate size were excised and DNA gel purified. The amplified fragments were then used as template to assemble the 1533 nt rebuilt HPV 45 L1 gene.

Following rebuild, the 1533 nt band was gel purified, ligated to pCR4 Blunt (Invitrogen) and *E. coli* TOP10 cells were transformed with the ligation mixture. Colonies were grown in 4 ml LB with ampicillin and plasmid DNA was extracted by standard miniprep techniques. The plasmid DNA was sequenced to confirm the presence of the desired changes for the 45 L1 rebuild. The 45 L1 R (rebuild) was re-amplified from pCR4Blunt-45 L1 R to add BamHI extensions to both ends plus a yeast 5'-non-translated leader sequence upstream of the ATG initiation codon. The amplified fragment was cloned as above and plasmid DNA was sequenced. The plasmid, pCR4 Blunt-45 L1 R (Bam), was digested with BamHI and DNA fragments were electrophoresed on an agarose gel. The ~1550 bp 45 L1 R (Bam) fragment was gel purified, ligated to BamHI-digested pGAL110 and transformed into TOP10F' *E. coli* (Invitrogen).

Colonies were screened by PCR for the HPV 45 L1 R insert in the correct orientation in pGAL110. Sequence and orientation were confirmed by DNA sequencing. Maxiprep plasmid DNA was prepared and used for the transformation of *S. cerevisiae* cells which had been made competent by spheroplasting. The transformed yeast were plated in Leu(–) sorbitol top-agar onto Leu(–) sorbitol plates, which were incubated inverted for 7 days. Colonies were streaked for clonal isolation on Leu(–) sorbitol plates. Isolated colonies were subsequently grown in 5 ml of 5× Leu(–) Ade(–) sorbitol with 1.6% glucose and 4% galactose in rotating tube cultures at 30° C. to induce L1 transcription and protein expression. After 48 hours, a culture volume equivalent to an $OD_{600}=10$ was pelleted, the supernatant was removed and the pellets were frozen and stored at –70° C.

EXAMPLE 3

RNA Preparation

Cell pellets of transformed yeast induced to express HPV 45 L1 by galactose induction were thawed on ice, suspended in 0.8 ml of Trizol reagent (Life Technologies, Gibco BRL) and incubated at room temperature for 5 minutes. One fifth volume of chloroform was added to the vial. It was then shaken vigorously for 15 seconds to mix and incubated at room temperature for 3 minutes. After a 5 minute centrifugation at 13 k rpms, the upper phase was collected and transferred to a new vial. 0.4 ml isopropanol was added and incubated at room temperature for 10 minutes. Centrifugation to pellet the RNA was performed at 13 k rpms for 10 minutes. The supernatant was decanted, the RNA pellet washed with 75% EtOH and centrifugation repeated. The supernatant was decanted and the RNA pellet allowed to air dry for 15 minutes followed by suspension in RNase-free water. Spectrophotometry was performed to determined the concentration of RNA in the sample using the assumption that an $A_{260}$ reading of 1=40 µg/ml RNA when the $A_{260/280}$ is 1.7-2.0.

EXAMPLE 4

Northern Blot Analysis

A 1.1% agarose formaldehyde gel was cast. Five and ten micrograms of RNA was combined with denaturing buffer (final concentrations: 6% formaldehyde, 50% formamide and 0.1× MOPS) and heated to 65° C. for 10 minutes. A one-tenth volume of gel loading buffer was added and the sample loaded onto the gel. Electrophoresis was performed at 75 volts in 1×MOPS buffer for ~3 hours. The gel was washed for 60 minutes in 10×SSC.

The RNA was transferred to a Hybond-N+ nylon membrane (Amersham Biosciences, Piscataway, N.J.) by capillary action over 16 hours in 10×SSC. The RNA was then fixed to the nylon membrane by cross-linking using the Stratagene UV Stratalinker (Stratagene, La Jolla, Calif.) auto-crosslink function. After fixing, the nylon membrane was allowed to air dry.

The Roche DIG High Prime DNA Labeling and Detection Kit I (F. Hoffmann-La Roche Ltd., Basel, Switzerland) was used to label 45 L1 R DNA sequences with DIG to be used as a probe to detect 45 L1 R RNA on the Northern blot. The pre-hybridization, hybridization and immunological development using an anti-DIG alkaline phosphatase conjugated antibody were performed per the manufacturer's recommendations. Briefly, the blot was pre-hybridized at 37° C. for 30 minutes with gentle shaking. The probe was denatured by heating to 95° C. for 5 minutes and quenching on ice. The probe was added to the hybridization solution and applied to the membrane for 4 hours at 44.6° C. with gentle shaking. The hybridization solution was then removed and the blot washed twice for 5 minutes in 2×SSC with 0.1% SDS at room temperature, followed by an additional wash at 65° C. with 0.5×SSC and 0.1% SDS. The blot was then blocked for 30 minutes and anti-DIG alkaline phosphatase conjugated antibody applied at a 1:5000 dilution for 30 minutes. The blot was washed and the presence of probe bound RNA determined by NBT/BCIP substrate detection of the alkaline phosphatase conjugated anti-DIG bound antibody.

Initial analysis of yeast expressing 45 L1 wt suggested that there was functional HPV 45 L1 transcription and translation; however, the sequence was rebuilt with yeast-preferred codon sequences to obtain an increased level of expression, useful for vaccine development. The rebuilt 45 L1 sequence was engineered to omit any possible premature transcription termination sites to ensure robust transcription. Northern blot analysis of the 45 L1 R transcript revealed that full-length transcripts were generated (FIG. 3).

EXAMPLE 5

HPV 45 L1 Protein Expression

Frozen yeast cell pellets of galactose-induced cultures equivalent to $OD_{600}=10$, were thawed on ice and suspended in 300 µl of PC buffer (100 mM $Na_2HPO_4$ and 0.5 M NaCl, pH 7.0) with 2 mM PMSF. Acid-washed 0.5 mm glass beads, were added, ~0.5 g/tube. The tubes were vortexed for 3 cycles of 5 minutes at 4° C. with a 1 minute break. 7.5 µl of 20% TritonX100 was added and vortex repeated for 5 minutes at 4° C. The tubes were placed on ice for 15 minutes, and then centrifuged for 10 minutes at 4° C. The supernate was transferred to a sterile microfuge tube, labeled as total yeast protein extract, dated and stored at −70° C.

EXAMPLE 6

Western Blot Analysis

Total yeast protein extract from twenty isolated yeast colonies for each 45 L1 construct were analyzed by Western blot to confirm expression of 45 L1 protein after galactose induction.

Ten micrograms of total yeast protein extract was combined with SDS-PAGE loading buffer and heated to 95° C. for 10 minutes. The proteins were loaded onto a 10% SDS-PAGE gel and electrophoresed in Tris-Glycine buffer. After protein separation, the proteins were Western transferred from the gel to nitrocellulose and the blot blocked in 1× diluent buffer (Kirkegaard and Perry Laboratories) for 1 hour at room temperature with rocking. The blot was washed three times and then incubated with a 1:2500 dilution of goat anti-trpE-HPV 45 L1 serum at room temperature for 16 hours. The blot was then washed three times and incubated with a 1:2500 dilution of anti-goat-HRP conjugated antibody for 1 hr. The blot was again washed three times and NBT/BCIP detection substrate applied (Kirkegaard and Perry Laboratories). Immunoreactive proteins were detected as purple bands on the blot.

Figure 4:
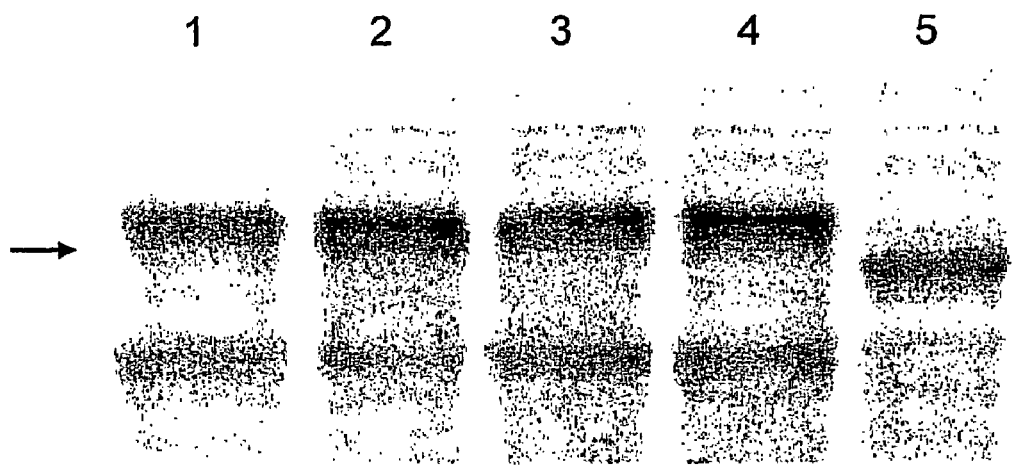
FIG. 4 shows a Western Blot of HPV 45 L1 wt and three HPV 45 L1 R isolates. Contents of the lanes are: 45 L1 wt (lane 1), 45 L1 R #4 (lane 2), 45 L1 R #7 (lane 3), 45 L1 R#11 (lane 4), HPV 16 L1 control (lane 5). Fifteen micrograms of total yeast protein extract were loaded into each lane of a 10% SDS-PAGE gel. A goat polyclonal anti-serum against a TrpE-HPV 45 L1 fusion protein was used to specifically identify the HPV 45 L1 protein. The arrow at the left indicates the 55 kDa position.

The results demonstrate that in all cases, the 45 L1 protein was detected as a distinct immunoreactive band on the nitrocellulose corresponding to approximately 57 kDa (FIG. 4). The 16 L1 protein, which is approximately 55 kDa, was included as a positive control, along with HPV L1-free total yeast protein extract as a negative control (data not shown).

EXAMPLE 7

ELISA Assay

The yeast cells expressing HPV 45 L1 were grown by a variety of methods including rotating tube cultures, shake flasks and fermenters. The yeast were lysed and protein extracts were made to determine the amount of HPV 45 L1 virus-like particles (VLPs) produced per microgram of total protein. A sandwich ELISA was designed to demonstrate HPV 45 L1 VLP expression.

The H18R.5 monoclonal antibody (mAb), which recognizes both HPV type 18 and 45 L1 VLPs, was used to bind the 45 L1 VLPs found in the yeast protein extracts. The unbound proteins were washed away and H45.10B11.A5, an HPV 45 L1 VLP type and conformational specific mAb, was applied as a detection antibody. True, conformationally correct, 45 L1 VLPs were bound and detection was facilitated by the use of an anti-mouse IgG1 HRP-conjugated antibody and TMB substrate.

Specifically, H18R.5 was used to coat the bottom of Immulon 4 HBX 96 well plates overnight at 4° C. The plates were washed three times with PBS and 0.05% Tween 20, followed by blocking with blocking solution (PBS+0.05% Tween 20+1% BSA). The plates were washed three times and antigens (total yeast cell lysates diluted in blocking solution to 100 µg/ml), were applied to row A in duplicate. Reference standards of purified HPV 45 L1 VLPs were applied to row A columns 1 and 2 at 3300 ng/ml in 100 µg/ml total yeast protein. The reference and test samples were then serially diluted two-fold down each column. After three hours at room temperature the excess antigen was removed by aspiration and the plates washed 3 times. Cell supernatant containing HPV 45 L1 VLP conformational specific mAb H45.10B11.A5 was diluted 1:80 in blocking solution and applied to each well for an hour at room temperature. The plates were washed three times and an anti-mouse IgG1 HRP-conjugated antibody diluted 1:8000 in blocking solution was applied for 1 hour at room temperature. The plates were washed and TMB (Pierce) applied for 5 minutes to detect HRP-conjugated antibody complexes. The detection reaction was stopped by the addition of 2M $H_2SO_4$. Plates were read at 450 nm wavelength and the concentration of HPV 45 L1 VLP was determined by comparison to the reference standards in ng VLP/µg total protein.

Figure 6:
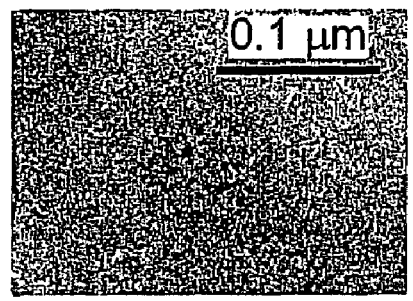
FIG. 6 shows a representative sample of HPV 45 VLPs composed of HPV 45 L1 R protein molecules, described herein, as visualized by transmission electron microscopy (see EXAMPLE 8). The bar represents approximately 100 nm.

A comparison between 45 L1 wt and two separate clones of 45 L1 R, all assayed in duplicate, is shown in FIG. 5. Rebuilt HPV 45 L1 VLP expression was approximately 2 fold higher than the results observed for 45 L1 wt (FIG. 6).

EXAMPLE 8

Transmission Electron Microscopy

To demonstrate that the 45 L1 protein was in fact self-assembling to form pentameric-L1 capsomers, which in turn self-assemble into virus-like particles, a partially purified 45 L1 R protein extract was analyzed by transmission EM.

Yeast cells were grown under small scale fermentation conditions, pelleted and the pellets were subjected to purification treatments. Pellet and clarified yeast extracts were analyzed by immunoblot to demonstrate L1 protein expression and retention through the purification procedure. Clarified yeast extracts were then subjected to centrifugation over a 45%-sucrose cushion and the resulting pellet suspended in buffer for analysis by transmission electron microscopy (EM).

A representative sample of the 45 L1 R VLPs produced is shown in FIG. 6. The diameter of the spherical particles in this crude sample ranged from between 40 and 60 nm with some particles displaying a regular array of capsomers.

The invention claimed is:

1. A nucleic acid molecule encoding an HPV45 L1 protein consisting of SEQ ID NO: 2, wherein said nucleic acid molecule comprises a nucleic acid sequence encoding SEQ ID NO: 2 which is codon-optimized for high expression in a yeast cell.

2. A vector comprising the nucleic acid molecule of claim 1.

3. A host cell comprising the vector of claim 2.

4. The host cell of claim 3, wherein the host cell is selected from the group consisting of: *Saccharomyces cerevisiae, Hansenula polymorpha, Pichia pastoris, Kluyveromyces fragilis, Kluyveromyces lactis*, and *Schizosaccharomyces pombe*.

5. The host cell of claim 4, wherein the host cell is *Saccharomyces cerevisiae*.

6. The nucleic acid molecule of claim 1, wherein the sequence of nucleotides comprises a sequence of nucleotides as set forth in SEQ ID NO: 1.

7. A vector comprising the nucleic acid molecule of claim 6.

8. A host cell comprising the vector of claim 7.

* * * * *